United States Patent
Hata et al.

(10) Patent No.: US 6,346,537 B1
(45) Date of Patent: *Feb. 12, 2002

(54) MEDICINAL COMPOSITION

(75) Inventors: Takehisa Hata, Nagaokakyo; Yuji Tokunaga, Sanda; Fumio Shimojo; Sumihisa Kimura, both of Kawanishi; Takeo Hirose, Kyoto; Satoshi Ueda, Kawanishi, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,672

(22) PCT Filed: Dec. 5, 1997

(86) PCT No.: PCT/JP97/04452

§ 371 Date: Jun. 4, 1999

§ 102(e) Date: Jun. 4, 1999

(87) PCT Pub. No.: WO98/24418

PCT Pub. Date: Jun. 11, 1998

(30) Foreign Application Priority Data

Dec. 6, 1996 (JP) .............................. 8-326618

(51) Int. Cl.$^7$ ................................................ A61K 31/44
(52) U.S. Cl. ........................ 514/294; 514/411; 424/452; 424/405; 424/502
(58) Field of Search ................................ 514/294, 411; 424/452, 405, 502

(56) References Cited

U.S. PATENT DOCUMENTS

| 4,916,138 A | 4/1990 | Ueda et al. |
| 5,215,995 A | 6/1993 | Honbo et al. |
| 5,368,865 A | 11/1994 | Asakura et al. |
| 5,601,844 A | 2/1997 | Kagayama et al. |
| 5,770,607 A | 6/1998 | Honbo et al. |
| 5,817,333 A | 10/1998 | Kagayama et al. |

FOREIGN PATENT DOCUMENTS

| EP | 240773 | 10/1987 | |
| JP | 62-277321 | 12/1987 | |
| JP | 7-291854 | * 11/1995 | ................. 514/302 |

* cited by examiner

*Primary Examiner*—James H. Reamer
(74) *Attorney, Agent, or Firm*—Oblon, Spivak, McClelland, Maier & Neustadt, P.C.

(57) ABSTRACT

To provide a pharmaceutical composition comprising a water-insoluble active substance, surfactant(s) and solid carrier(s), which is improved in dissolution and oral absorption characteristics.

8 Claims, 1 Drawing Sheet

FIG. 1

MEDICINAL COMPOSITION

TECHNICAL FIELD

This invention relates to a pharmaceutical composition comprising a water-insoluble medicinally active substance, surfactant(s) and solid carrier(s), which has very satisfactory dissolution property, oral absorbability and so on. The pharmaceutical composition of the present invention can be used in the field of medical care.

BACKGROUND ART

To provide a pharmaceutical preparation of a water-insoluble medicinally active substance, particularly a pharmaceutical composition for oral administration, it is common practice to cause a polymer such as hydroxypropylmethylcellulose and the medicinally active substance to form a solid dispersion, and typically such a solid dispersion has been proposed for the under-mentioned FK506 (or FR-900506) which is well known to have a potent immunosuppressive activity but be insoluble in water (Japanese Tokkyo Kokai Koho S62-277321).

| | |
|---|---|
| Generic name: | tacrolimus |
| Chemical name: | 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone |

However, it is generally acknowledged that the absorption of such a solid dispersion after oral administration has a tendency toward some variation. The inventors of this invention did intensive research and have succeeded in developing a pharmaceutical composition which, even in cases where the active ingredient is a substance which is insoluble in water (i.e. a water-insoluble medicinally active substance), assures very satisfactory characteristics such as favorable dissolution property, high absorption, and/or less variation in said absorption.

DISCLOSURE OF THE INVENTION

This invention is essentially directed to a pharmaceutical composition comprising a water-insoluble medicinally active substance, surfactant (s) and solid carrier(s) and to a process for producing said composition. This invention is now described in detail.

The "water-insoluble medicinally active substance" which can be used in the pharmaceutical composition of the instant application includes any and all medicinally active substances that are insoluble in water, such as, for example, tricyclic compounds of the formula (I), represented by FK506 mentioned above, and their pharmaceutically acceptable salts.

(I)

(wherein each of adjacent pairs of $R^1$ and $R^2$, $R^3$ and $R^4$ or $R^5$ and $R^6$ independently (a) is two adjacent hydrogen atoms, or
(b) may form another bond formed between the carbon atoms to which they are attached,
and further, $R^2$ may be an alkyl group;
$R^7$ is a hydrogen atom, a hydroxy group, a protected hydroxy group or an alkoxy group, or an oxo group together with $R^1$;
each of $R^8$ and $R^9$ is independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;
X is an oxo group, (a hydrogen atom and a hydroxy group), (a hydrogen atom and a hydrogen atom), or a group represented by the formula —CH$_2$O—;
Y is an oxo group, (a hydrogen atom and a hydroxy group), (a hydrogen atom and a hydrogen atom), or a group represented by the formula N—NR$^{11}$R$^{12}$ or N—OR$^3$;
each of $R^{11}$ and $R^{12}$ is independently a hydrogen atom, an alkyl group, an aryl group or a tosyl group;
each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;
each of $R^{20}$ and $R^{21}$ is independently an oxo group or ($R^{20}$a and a hydrogen atom) or ($R^{21}$a and a hydrogen atom) in which each of $R^{20}$a and $R^{21}$a is independently a hydroxy group, an alkoxy group or a group represented by the formula —OCH$_2$OCH$_2$CH$_2$OCH$_3$, or $R^{21}$a is a protected hydroxy group, or $R^{20}$a and $R^{21}$a may together represent an oxygen atom in an epoxide ring;

n is an integer of 1 or 2; and in addition to the above definitions, Y, $R^{10}$ and R23, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl and a group of the formula —$CH_2Se(C_6H_5)$).

The compound (I) and its pharmaceutically acceptable salt are known as immunosuppressants (Japanese Tokkyo Kokai Koho S61-148181, EP0323042), and FK506, inparticular, has already been put to use in the therapy and prophylaxis of rejection reactions by transplantation of organs such as the heart, liver, kidney, bone marrow, skin, cornea, lung, pancreas, small intestine, muscle, nerve, limb, etc. and of various autoimmune diseases.

The above-mentioned compound (I) and its pharmaceutically acceptable salt can be provided by the same methods as disclosed in the two patent gazettes mentioned above. Particularly the tricyclic compounds produced by cultivation of *Streptomyces tsukubaensis* No. 9993 (FERM-BP 927) or *Streptomyces hygroscopicus* subsp. *yakushimaensis* No. 7238 (FERM-BP 928) have been given the identification numbers FR-900506, FR-900520, FR-900523, and FR-900525 (Japanese Tokkyo Kokai Koho S61-148181).

First, the definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" are 1- (lower alkylthio) (lower) alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenyl-silyl, etc.), more preferably tri ($C_1$–$C_4$) alkylsilyl group and $C_1$–$C_4$ alkyl-diphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, arboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri (lower)alkylsilyl(lower)alkoxycarbonyl(lower) alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$) alkyls at the cycloalkyl moiety, camphorsulfonyl group, carboxy($C_1$–$C_4$) alkylcarbamoyl group, tri($C_1$–$C_4$) alkylsilyl ($C_1$–$C_4$)alkoxycarbonyl($C_1$–$C_4$)alkylcarbamoyl group, benzoyl group optionally having one or two nitro groups, benzenesulfonyl group having halogen, or phenyl ($C_1$–$C_4$)alkanoyl group having $C_1$–$C_4$alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The pharmaceutically acceptable salt of the compound (I) includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the compound (I), it is to be understood that there may be conformers and one or more stereoisomers such as optical and geometrical isomers due to asymmetric carbon atom(s) and double bond(s), and such conformers and isomers are also included within the scope of the present invention.

The compound of the formula (I) and its salt can be in the form of a solvate, which is included within the scope of the present invention. The solvate preferably include a hydrate and an ethanolate.

The preferred examples of the tricyclic compound (I) is the one, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

each of $R^{20}$ and $R^{21}$ is independently ($R^{20}$a and a hydrogen atom) or ($R^{21}$a and a hydrogen atom) in which each of $R^{20}$a and $R^{21}$a is a hydroxy group or an alkoxy group, or $R^{21}$a is a protected hydroxy group; and n is an integer of 1 or 2. FK506 is the most preferable compound belonging to the tricyclic compound (I). Other preferable compounds are listed hereinbelow.

1,14-Dihydroxy-12-[2-(4-hydroxy-3-methoxycyclohexyl)-1-methylvinyl]-23,25-dimethoxy-13,17,19,21,27-pentamethyl-11,28-dioxa-4-azatricyclo[22.3.1.0$^{4,9}$]octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone,

17-allyl-1,14-dihydroxy-23,25-dimethoxy-13,19,21,27-tetramethyl-12-[2-[4-(3,5-dinitrobenzoyloxy)-3-methoxycyclo-hexyl]-1-methylvinyl]-11,28-dioxa-4-azatricyclo[22.3.1.0$^{4,9}$]octacos-18-ene-2,3,10,16-tetraone, 17-allyl-12-[2-[4-[(−)-2-trifluoromethyl-2-methoxy-2-phenylacetoxy]-3-methoxycyclohexyl]-1-methylvinyl]-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone.

17-ethyl-1,14-dihydroxy-12-[2-(4-hydroxy-3-methoxycyclo-hexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR900520), and 17-ethyl-1,14,20-trihydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

As other examples of the water-insoluble medicinally active substance which can be used in the present invention, there can be mentioned the following urea derivative (II) and its pharmacologically acceptable salt.

(II)

[wherein $R^{24}$ represents aryl optionally substituted by halogen, nitro, amino, lower alkylamino, lower alkoxy or acylamino, $R^{25}$ represents hydrogen; alkyl; cycloalkyl; or lower alkyl substituted by cyclo(lower) alkyl, cyclo(lower)alkenyl, heterocyclyl, or aryl which may have substituents selected from the class consisting of halogen, hydroxy, and lower alkoxy; $R^{26}$ represents hydrogen, lower alkyl, or aryl which may be substituted by halogen, nitro, amino or lower alkylamino;

$R^{27}$ represents hydrogen, halogen, lower alkyl, lower alkoxy, or aryl which may be substituted by halogen;

$R^{28}$ represents hydrogen, halogen, lower alkyl or aryl,

A represents a single bond or lower alkylene,

Z represents O, S, or NH]

The various definitions used in the general formula (II) representing the above urea derivative and the preferred examples are now described in detail.

The term "lower" is used here in reference to any group containing 1 to 6 carbon atoms unless otherwise specified.

The term "lower" as used for said "cyclo(lower)alkyl" means a carbon number of 3 to 6. The term "lower" as used for said "cyclo(lower)alkenyl" means a carbon number of 3 to 6.

The term "alkyl" is used here to encompass both lower alkyl and higher alkyl groups.

The term "cycloalkyl" may mean both cyclo(lower)alkyl and cyclo(higher)alkyl.

The preferred "lower alkyl" and "lower alkyl" moiety of said "lower alkylamino" or "ar (lower) alkyl" includes straight-chain or branched alkyl such as methyl, ethyl, propyl, isopropyl, butyl, isobutyl, tert-butyl, pentyl, isopentyl, and hexyl. Particularly preferred lower alkyl groups are methyl, ethyl, propyl, isopropyl, pentyl, and isopentyl.

The preferred "cyclo(lower)alkyl" includes cyclopropyl, cyclobutyl, cyclopentyl, and cyclohexyl. The preferred "cyclo(lower)alkenyl" includes cyclopropenyl, cyclobutenyl, cyclopentenyl, and cyclohexenyl.

The term "higher" as used herein means a carbon number of 7 to 20 unless otherwise indicated. The preferred "higher alkyl" includes such straight-chain and branched alkyl groups as heptyl, octyl, nonyl, decyl, undecyl, dodecyl, tridecyl, tetradecyl, pentadecyl, hexadecyl, heptadecyl, octadecyl, nonadecyl, eicosyl, methylheptyl, methyloctyl, methylnonyl, methyldecyl, ethylheptyl, ethyloctyl, ethylnonyl, and ethyldecyl. The more preferred are alkyl groups of 7 to 10 carbon atoms and the most preferred is heptyl or nonyl.

The preferred "cyclo(higher)alkyl" includes cycloheptyl, cyclooctyl, cyclononyl, cyclodecyl, cycloundecyl, cyclotridecyl, cyclotetradecyl, cyclopentadecyl, cyclohexadecyl, cycloheptadecyl, cyclooctadecyl, cyclononadecyl, and cycloeicosyl. Particularly preferred are those containing 7 to 10 carbon atoms. The most preferred is cycloheptyl.

The preferred "lower alkoxy" includes straight-chain or branched alkoxy groups such as methoxy, ethoxy, propoxy, isopropoxy, butoxy, isobutoxy, tert-butoxy, pentyloxy, hexyloxy, etc., with methoxy being the most useful.

The preferred "halogen" includes fluorine, chlorine, bromine, and iodine, with fluorine or chlorine being particularly useful.

The preferred "aryl" includes phenyl, naphthyl, and phenyl substituted by lower alkyl (e.g. tolyl, xylyl, mesityl, cumenyl, diisopropylphenyl, etc.). The more preferred is phenyl or phenyl substituted by lower alkyl.

The preferred "lower alkylamino" includes mono- or di-(lower alkyl) amino groups such as methylamino, ethylamino, dimethylamino, diethylamino, etc., with dimethylamino being particularly useful. The preferred "ar(lower)alkyl" includes but is not limited to phenyl (lower) alkyl (e.g. benzyl, phenethyl, phenylpropyl, etc.), benzhydryl, trityl, tolylmethyl, xylylmethyl, mesitylmethyl, and cumenylmethyl, with phenyl(lower)alkyl being particularly preferred. The most useful is benzyl.

The preferred "lower alkylene" includes straight-chain or branched alkylene groups such as, for example, methylene, ethylene, trimethylene, propylene, tetramethylene, pentamethylene, hexamethylene, and ethylethylene. The aryl for $R^{24}$, $R^{26}$, and $R^{27}$ may be substituted by 1~5 of the above-mentioned substituent groups. The preferred number of substituents is 1, 2, or 3.

The aryl as a substituent on the lower alkyl for $R^{25}$ may be substituted by 1~5 of said substituent groups, and the preferred number of substituents is 1, 2, or 3.

The preferred "aryl substituted by halogen" includes chlorophenyl, dichlorophenyl, difluorophenyl, trichlorophenyl, and trifluorophenyl.

The preferred "heterocyclic group (heterocyclyl)" includes monocyclic or polycyclic hetero-ring residues, whether saturated or unsaturated, each containing at least one hetero-atom selected from among nitrogen, oxygen, and sulfur.

The preferred "heterocyclic group" as defined above includes 3- through 8-membered, preferably 5- or 6-membered, unsaturated monocyclic hetero systems each containing 1~4 nitrogen atoms, such as pyrrolyl, imidazolyl, pyrazolyl, pyridyl, pyridyl-N-oxide, dihydropyridyl, tetrahydropyridyl, pyrimidyl, pyrazinyl, pyridazinyl, triazinyl, triazolyl, tetrazinyl, tetrazolyl, etc.; 3- through 8-membered, preferably 5- or 6-membered, saturated monocyclic hetero systems each containing 1~4 nitrogen atoms such as pyrrolidinyl, imidazolidinyl, piperidino, piperazinyl, etc., unsaturated fused heterocyclic residues each containing 1~5 nitrogen atoms such as indolyl, isoindolyl, indolidinyl, benzimidazolyl, quinolyl, isoquinolyl, indazolyl, benzotriazolyl, etc.;

- 3- through 8-membered unsaturated monocyclic hetero systems each containing 1 or 2 oxygen atoms and 1~3 nitrogen atoms, such as oxazolyl, isoxazolyl, oxadiazolyl, etc.; 3- through 8-membered saturated monocyclic hetero systems each containing 1 or 2 oxygen atoms and 1 to 3 nitrogen atoms, such as morpholino, sydnonyl, etc.; unsaturated fused heterocyclic groups each containing 1 or 2 oxygen atoms and 1 to 3 nitrogen atoms, such as benzoxazolyl, benzoxadiazolyl, etc.;
- 3- through 8-membered unsaturated monocyclic hetero systems each containing 1 or 2 sulfur atoms and 1 to 3 nitrogen atoms, such as thiazolyl, isothiazolyl, thiadiazolyl, etc.; 3- through 8-membered unsaturated monocyclic hetero systems each containing 1 or 2 sulfur atoms, such as thienyl; unsaturated fused heterocyclic groups each containing 1 or 2 sulfur atoms and 1 to 3 nitrogen atoms, such as benzothiazolyl, benzothiadiazolyl, etc.; 3- through 8-membered unsaturated monocyclic hetero systems each containing 1 oxygen atom, such as furyl; unsaturated fused heterocyclic groups each containing 1 or 2 sulfur atoms, such as benzothienyl; and unsaturated fused heterocyclic groups each containing 1 or 2 oxygen atoms, such as benzofuranyl.

Preferably, the heterocyclic group is pyridyl or furyl.

The preferred acyl moiety of said "acylamino" includes carboxy; esterified carboxy; carbamoyl optionally having substituent groups selected from the class consisting of lower alkyl, cyclo(lower)alkyl, aryl, and hydroxy; lower alkanoyl; heterocyclylcarbonyl; and lower alkylsulfonyl; among others.

The esterified carboxy includes but is not limited to substituted or unsubstituted lower alkoxycarbonyl (e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.), substituted or unsubstituted aryloxycarbonyl ((e.g. phenoxycarbonyl, 4-nitrophenoxycarbonyl, 2-naphthyloxycarbonyl, etc.), and substituted or unsubstituted ar(lower)alkoxycarbonyl (e.g. benzyloxycarbonyl, phenethyloxy-carbonyl, benzhydryloxycarbonyl, 4-nitrobenzyloxycarbonyl, etc.).

The "lower alkanoyl" includes but is not limited to formyl, acetyl, propionyl, butyryl, isobutyryl, valeryl, isovaleryl, pivaloyl, and hexanoyl. Particularly preferred is acetyl.

The heterocyclic moiety of said "heterocyclylcarbonyl" includes the same groups as mentioned for said "heterocyclic group".

The "lower alkylsulfonyl" includes but is not limited to methylsulfonyl, ethylsulfonyl, and propylsulfonyl, with methylsulfonyl being particularly useful.

The preferred "acylamino" includes lower alkanoylamino and lower alkylsulfonylamino. Particularly preferred is acetylamino or methylsulfonylamino.

The preferred pharmacologically acceptable salt of compound (II) includes nontoxic salts of the conventional types, such as inorganic acid addition salts (e.g. hydrochloride, hydrobromide, sulfate, phosphate, etc.), organic acid addition salts (e.g. formate, acetate, trifluoroacetate, maleate, tartrate, methanesulfonate, benzenesulfonate, toluenesulfonate, etc.), and alkali metal salts (e.g. sodium salt, potassium salt, etc.).

The above-mentioned urea derivative (II) and pharmacologically acceptable salt thereof are already known from inter alia Japanese Tokkyo Kokai Koho H5-140102, as compounds which are useful for prevention and treatment of hypercholesterolemia, hyperlipidemia, and atherosclerosis, and can be produced by the method described therein.

The surfactant which is to be used in accordance with this invention is now described.

The surfactant that can be used includes pharmaceutically acceptable natural or synthetic surfactants. As natural surfactants, a variety of surfactants of the animal origin or of the vegetable origin can be employed. Synthetic surfactants can be used regardless of whether they are cationic, anionic, or nonionic.

To mention preferred examples, the following surfactants can be employed.

Polyoxyethylene alkyl ethers (polyoxyethylene oleyl ethers, polyoxyethylene stearyl ether, polyoxyethylene cetyl ether, polyoxyethylene lauryl ether (Lauromacrogol (Japanese Pharmacopoeia), etc.)

Polyoxyethylene sorbitan fatty acid esters (Tween 20™, Tween 40™, Tween 6™, Tween 65™, Tween $_{80}$™, etc.)

Polyoxyethylene glyceryl fatty acid monoesters (polyoxyethylene glyceryl monostearate etc.)

Polyoxyethylene propylene glycol fatty acid monoesters (polyoxyethylene propylene glycol monostearate, polyoxyethylene propylene glycol monooleate, etc.)

Polyoxyethylene sorbitol fatty acid esters (polyoxyethylene sorbitol tetraoleate, polyoxyethylene sorbitol hexastearate, polyoxyethylene sorbitol monolaurate, polyoxyethylene sorbitol beeswax, etc.)

Polyoxyethylene derivatives of natural oils and waxes (polyoxyethylene castor oil, polyoxyethylene hydrogenated castor oil (HCO-40, HCO-60, Cremophor RH40, Cremophor RH60, etc.; all trademarks), polyoxyethylene lanolin, etc.)

Polyethylene glycol fatty acid esters (polyethylene glycol monooleate, polyethylene glycol monostearate (polyoxyl stearate 40 (Japanese Pharmacopoeia), etc.), polyethylene glycol monolaurate, etc.)

Propylene glycol fatty acid mono- or diesters (propylene glycol monocaprylate (Sefsol-218™ etc.), propylene glycol dicaprylate (Sefsol-228™ etc.), propylene glycol monocaprate, propylene glycol dicaprate (Sefsol-220™ etc.), propylene glycol monolaurate, propylene glycol monoisooctanoate (Sefsol-2126™ etc.), propylene glycol diisooctanoate (Sefsol-2226™ etc.), Miglyol 840™, etc.)

Sorbitan fatty acid esters (sorbitan monooleate (Span 80™ etc.), sorbitan monostearate (Span 60™ etc.), sorbitan monopalmitate (Span 40™ etc.), sorbitan monolaurate (Span 20™ etc.), sorbitan monocaprylate (Sefsol-418™ etc.), etc.)

Sucrose fatty acid esters (DK-SS, DK-F160, DK-F140, DK-F110, all trademarks of Daiichi Kogyo Seiyaku, etc.)

Polyoxyethylene-polyoxypropylene copolymer and block copolymer surfactants (Pluronic F87™, Pluronic F127™, Pluronic F68™, Pluronic L44™, Pluronic P123™, Pluronic P85™, Poloxamer 188™, Poloxamer 235™, Poloxamer 403™, Poloxamer 407™, etc.)

Sulfuric acid alkyl ester salts (sodium lauryl sulfate etc.)

Phospholipids (purified egg yolk lecithin, purified soybean lecithin, etc.)

Bile acid salts (sodium taurocholate, sodium glycocholate, etc.),

Fatty acids (oleic acid, linoleic acid, etc.)

Monohydric alcohol fatty acid esters (isopropyl myristate, butyl myristate, isocetyl myristate, octyldodecyl myristate, isopropyl palmitate, isostearyl palmitate, isopropyl isostearate, isocetyl isostearate, butyl stearate, isocetyl stearate, cetyl isooctanoate, ethyl linoleate, isopropyl linoleate, hexyl laurate, ethyl oleate, decyl oleate, oleyl oleate, octyldodecyl myristate, hexyldecyl dimethyloctanoate, octyldodecyl neodecanoate, etc.)

Ethylene glycol fatty acid esters (ethylene glycol monocaprylate (Sefsol-118™ etc.), ethylene glycol dicaprylate (Sefsol-128™ etc.), ethylene glycol monoisooctanoate (Sefsol-1126™ etc.), ethylene glycol diisooctanoate (Sefsol-1226™ etc.), etc.

Other polyhydric alcohol fatty acid esters [tetraglycerin monocaprylate (Sefsol-618™ etc.), tetraglycerin hexacaprylate (Sefsol-668™ etc.), etc.]

Dibasic acid diesters (diisopropyl adipate, diisobutyl adipate, diethyl sebacate, diisopropyl sebacate, diethyl phthalate, etc.)

Alcohols (oleyl alcohol, cetanol, stearyl alcohol, etc.)

Others (squalane, squalene, etc.).

In accordance with the present invention, the above-mentioned surfactants can be used each alone or in combination.

More preferable surfactants are polyoxyethylene hydrogenated castor oil, sucrose fatty acid esters, propylene glycol fatty acid mono- or di-esters, polyoxyethylene sorbitan fatty acid esters, and so on, and the most preferable one is the combinaiton of polyoxyethylene hydrogenated castor oil and propylene glycol fatty acid mono- or di-esters.

The term "solid dispersion" used in the present invention is the well known one, and which is a solid one wherein a medicinally active substance is being dispersed as an amorphous form in an inert carrier or matrix thereof as explained in, for example, J. Pharm. Sci. 60(9) p1281- (1971), incorporated by reference.

The solid carrier for use in the present invention includes any and all pharmaceutically acceptable solid carriers which can form a solid dispersion with a water-insoluble medicinally active substance, but is preferably selected from among the following substances.

Polymers [polyvinylpyrrolidone, polyvinylpolypyrrolidone, cellulose polymers (hydroxypropylmethylcellulose, hydroxypropylmethylcellulose phthalate, methylcellulose, ethylcellulose, carboxymethylcellulose sodium, hydroxyethylcellulose, hydroxypropylcellulose, cystalline cellulose, etc.), pectin, cyclodextrins, galactomannan, polyethylene glycol with a mean molecular weight of not less than 4000, gelatin, etc.]

Saccharides (dextrose, sucrose, galactose, sorbitol, maltose, xylitol, mannitol, lactose, etc.)

Acids (citric acid, succinic acid, etc.)

Others (light anhydrous silicic acid, pentaerythritol, pentaerythrytyl tetracetate, urea, hydroxyalkylxanthines, urethane, etc.)

Incidentally, those carriers can be used each alone or in combination. Preferable solid carriers are water-soluble ones, such as water-soluble polymers (e.g., cellulose polymers, polyvinylpyrrolidone, and so on); saccharides; light anhydrous silicic acid; and so on. And most preferable one is hydroxypropylmethylcellulose, polyvinylpyrrolidone, lactose, light anhydrous silicic acid, or their combination.

Optionally in addition to the above components, the conventional excipients (e.g. starch, etc), disintegrators (e.g. croscarmellose sodium, carboxymethylcellulose calcium, low substituted hydroxypropylcellulose, starch glycolate sodium, microcrystalline cellulose, crospovidone, etc.), coloring agents, sweeteners, flavors, diluents, antioxidant (e.g., vitamin E, etc) and lubricants (e.g., synthetic aluminum silicate, magnesium stearate, calcium stearate, talc, etc.) can be incorporated.

Meanwhile, the technology for manufacturing the pharmaceutical composition of the invention is now described.

The water-insoluble medicinally active substance and the surfactant are thoroughly dissolved in organic solvent(s) (e.g. ethanol) and a suitable amount of the solid carrier is added thereto. Then the mixture is kneaded well. After removing the organic solvent therefrom, the resultant residue is dried and pulverized to provide a solid pharmaceutical composition of the invention. In the kneading procedure referred to above, excipient(s) and disintegrator(s), such as low substituted hydroxypropylcellulose (L-HPC-21), may be further added where necessary.

While the effective dosage of said water-insoluble medicinally active substance depends on the type of the said substance, the patient's age, type of disease, severity of illness, and other factors, a daily dose of the active substance is about 0.01~1000 mg, preferably 0.05~500 mg, and more preferably, 0.1~100 mg for therapeutic purposes. The average unit dose may be generally about 0.1 mg, 0.5 mg, 1 mg, 5 mg, 10 mg, 50 mg, 100 mg, 250 mg, or 500 mg.

The proportions of the respective components of the pharmaceutical composition of the present invention are preferably selected according to their species but the following formulas may be mentioned as preferred examples.

The recommended proportion of said water-insoluble medicinally active substance relative to the total composition is 0.01~20% and preferably 0.1~10%.

The preferable weight ratio of the water-insoluble medicinally active substance, the surfactant and the solid carrier is 1:0.1~100:1~300, and more preferable one is 1:1~50:5~150. The most preferable one is 1:4~40:10~100.

Further, it is more preferable to add disintegrators as a component(s). In that case, the ratio of the said disintegrators among the total weight is 1–60%, and the more preferable one is 2–30%.

The following examples are intended to describe the invention in further detail and should not be construed as limiting the scope of the invention.

EXAMPLE 1 (Composition A)

Using bulk powders of N-benzyl-N-[3-(4-chlorophenyl)-5-methylbenzofuran-2-ylmethyl]-N'-(2,4,6-trifluorophenyl) urea (hereinafter referred to briefly as compound M) as prepared in the same manner as Example 6 (2) of Japanese Tokkyo Kokai Koho H5-140102, the following composition was provided.

| | |
|---|---|
| Compound M bulk | 10 mg |
| Propylene glycol monocaprylate (Sefsol-218 ™) | 60 mg |
| Sucrose fatty acid ester (DK-SS ™) | 100 mg |
| Hydroxypropylmethylcellulose (TC-5RW ™) | 330 mg |
| Low substituted hydroxypropylcellulose (L-HPC-21 ™) | 500 mg |
| Total | 1000 mg |

Compound M bulk powders (100 mg), propylene glycol monocaprylate (0. 6 g) and sucrose fatty acid ester (1 g) were added into ethanol (25 ml) and dissolved thoroughly. To this solution, was added hydroxypropylmethylcellulose (3.3 g) and then it was allowed to swell sufficiently. After that, it was kneaded and added low substituted hydroxypropylcellulose (5 g), and further kneaded. The resultant mixture was transferred to a stainless steel tray and was dried in vacuo for 24 hours, and then pulverized in amortar. The pulverized powder was sieved through a 32-mesh screen and was dried in vacuo for 24 hours again to provide Composition A.

The following compositions of Examples 2 and 3 were respectively prepared by using the same procedure as described in Example 1.

EXAMPLE 2

| | | |
|---|---|---|
| (1) | FK506 | 1 mg |
| | Polyoxyethylene hydrogenated castor oil | 4 mg |
| | Polyvinylpyrrolidone | 95 mg |
| | Total | 100 mg |
| (2) | FK506 | 1 mg |
| | Polyoxyethylene hydrogenated castor oil | 4 mg |
| | Hydroxypropylmethylcellulose | 95 mg |
| | Total | 100 mg |
| (3) | FK506 | 1 mg |
| | Polyoxyethylene 20 sorbitan monooleate (Tween 80) | 10 mg |
| | Lactose | 89 mg |
| | Total | 100 mg |
| (4) | FK506 | 1 mg |
| | Polyoxyethylene 20 sorbitan monooleate | 10 mg |
| | Hydroxypropylmethylcellulose | 89 mg |
| | Total | 100 mg |
| (5) | FK506 | 1 mg |
| | Polyoxyethylene hydrogenated castor oil | 4 mg |
| | Propylene glycol monocaprylate | 10 mg |
| | Lactose | 85 mg |
| | Total | 100 mg |

EXAMPLE 3

| | | |
|---|---|---|
| (1) | FK506 | 1 mg |
| | Polyoxyethylene hydrogenated castor oil | 4 mg |
| | Polyvinylpyrrolidone | 50 mg |
| | Lactose | 45 mg |
| | Total | 100 mg |
| (2) | FK506 | 1 mg |
| | Polyoxyethylene hydrogenated castor oil | 4 mg |
| | Hydroxypropylmethylcellulose | 50 mg |
| | Lactose | 45 mg |
| | Total | 100 mg |
| (3) | FK506 | 1 mg |
| | Polyoxyethylene 20 sorbitan monooleate | 10 mg |
| | Polyvinylpyrrolidone | 50 mg |
| | Lactose | 39 mg |
| | Total | 100 mg |
| (4) | FK506 | 1 mg |
| | Polyoxyethylene 20 sorbitan monooleate | 10 mg |
| | Hydroxypropylmethylcellulose | 50 mg |
| | Lactose | 39 mg |
| | Total | 100 mg |
| (5) | FK506 | 1 mg |
| | Polyoxyethylene hydrogenated castor oil | 4 mg |
| | Propylene glycol monocaprylate | 10 mg |
| | Polyvinylpyrrolidone | 50 mg |
| | Lactose | 35 mg |
| | Total | 100 mg |
| (6) | FK506 | 1 mg |
| | Polyoxyethylene hydrogenated castor oil | 6 mg |
| | Propylene glycol monocaprate | 10 mg |
| | Polyvinylpyrrolidone | 50 mg |
| | Lactose | 33 mg |
| | Total | 100 mg |
| (7) | FK506 | 1 mg |
| | Polyoxyethylene hydrogenated castor oil | 4 mg |
| | Propylene glycol monolaurate | 10 mg |
| | Polyvinylpyrrolidone | 50 mg |
| | Lactose | 35 mg |
| | Total | 100 mg |
| (8) | FK506 | 1 mg |
| | Polyoxyethylene hydrogenated castor oil | 4 mg |
| | Propylene glycol dicaprylate | 10 mg |

|      |                                      |         |
|------|--------------------------------------|---------|
|      | Polyvinylpyrrolidone                 | 50 mg   |
|      | Lactose                              | 35 mg   |
|      | Total                                | 100 mg  |
| (9)  | FK506                                | 1 mg    |
|      | Polyoxyethylene hydrogenated castor oil | 4 mg |
|      | Propylene glycol monocaprylate       | 5 mg    |
|      | Propylene glycol dicaprylate         | 5 mg    |
|      | Polyvinylpyrrolidone                 | 50 mg   |
|      | Lactose                              | 35 mg   |
|      | Total                                | 100 mg  |
| (10) | FK506                                | 1 mg    |
|      | Polyoxyethylene hydrogenated castor oil | 8 mg |
|      | Propylene glycol monocaprylate       | 10 mg   |
|      | Hydroxypropylmethylcellulose         | 50 mg   |
|      | Lactose                              | 31 mg   |
|      | Total                                | 100 mg  |
| (11) | FK506                                | 1 mg    |
|      | Polyoxyethylene hydrogenated castor oil | 4 mg |
|      | Propylene glycol monocaprate         | 10 mg   |
|      | Hydroxypropylmethylcellulose         | 50 mg   |
|      | Lactose                              | 35 mg   |
|      | Total                                | 100 mg  |
| (12) | FK506                                | 1 mg    |
|      | Polyoxyethylene hydrogenated castor oil | 4 mg |
|      | Propylene glycol monolaurate         | 10 mg   |
|      | Hydroxypropylmethylcellulose         | 50 mg   |
|      | Lactose                              | 35 mg   |
|      | Total                                | 100 mg  |
| (13) | FK506                                | 1 mg    |
|      | Polyoxyethylene hydrogenated castor oil | 4 mg |
|      | Propylene glycol dicaprylate         | 10 mg   |
|      | Hydroxypropylmethylcellulose         | 50 mg   |
|      | Lactose                              | 35 mg   |
|      | Total                                | 100 mg  |
| (14) | FK506                                | 1 mg    |
|      | Polyoxyethylene hydrogenated castor oil | 4 mg |
|      | Propylene glycol monocaprylate       | 5 mg    |
|      | Propylene glycol dicaprylate         | 5 mg    |
|      | Hydroxypropylmethylcellulose         | 50 mg   |
|      | Lactose                              | 35 mg   |
|      | Total                                | 100 mg  |
| (15) | FK506                                | 1 mg    |
|      | Purified soybean lecithin            | 10 mg   |
|      | Polyvinylpyrrolidone                 | 50 mg   |
|      | Lactose                              | 39 mg   |
|      | Total                                | 100 mg  |
| (16) | FK506                                | 1 mg    |
|      | Purified soybean lecithin            | 10 mg   |
|      | Hydroxypropylmethylcellulose         | 50 mg   |
|      | Lactose                              | 39 mg   |
|      | Total                                | 100 mg  |
| (17) | FK506                                | 1 mg    |
|      | Polyoxyethylene hydrogenated castor oil | 4 mg |
|      | Propylene glycol monocaprylate       | 10 mg   |
|      | Polyvinylpyrrolidone                 | 50 mg   |
|      | Lactose                              | 20 mg   |
|      | Croscarmellose sodium                | 15 mg   |
|      | Total                                | 100 mg  |
| (18) | FK506                                | 1 mg    |
|      | Polyoxyethylene hydrogenated castor oil | 4 mg |
|      | Propylene glycol monocaprylate       | 10 mg   |
|      | Hydroxypropylmethylcellulose         | 50 mg   |
|      | Lactose                              | 20 mg   |
|      | Croscarmellose sodium                | 15 mg   |
|      | Total                                | 100 mg  |
| (19) | FK506                                | 0.2 mg  |
|      | Propylene glycol monocaprylate       | 5 mg    |
|      | Sucrose fatty acid ester             | 2 mg    |
|      | Hydroxypropylmethylcellulose         | 60 mg   |
|      | Low substituted hydroxypropylcellulose | 32.8 mg |
|      | Total                                | 100 mg  |
| (20) | FK506                                | 2 mg    |
|      | polyoxyethylene hydrogenated castor oil | 4 mg |
|      | Propylene glycol monocaprylate       | 10 mg   |
|      | Polyvinylpyrrolidone                 | 20 mg   |
|      | light anhydrous silicic acid         | 10 mg   |
|      | crospovidone                         | 5 mg    |
|      | corn starch                          | q.s.    |
|      |                                      | 120 mg  |
| (21) | FK506                                | 1 mg    |
|      | polyoxyethylene hydrogenated castor oil | 4 mg |
|      | Propylene glycol monocaprylate       | 10 mg   |
|      | Polyvinylpyrrolidone                 | 30 mg   |
|      | crospovidone                         | 5 mg    |
|      | calcium stearate                     | 0.24 mg |
|      | corn starch                          | q.s.    |
|      |                                      | 120 mg  |
| (22) | FK506                                | 3 mg    |
|      | polyoxyethylene hydrogenated castor oil | 4 mg |
|      | Propylene glycol monocaprylate       | 10 mg   |
|      | Polyvinylpyrrolidone                 | 30 mg   |
|      | crospovidone                         | 5 mg    |
|      | corn starch                          | q.s.    |
|      | α-tocopherol                         | 0.3 mg  |
|      |                                      | 120 mg  |

EXAMPLE 4 (Dissolution Test)

A dissolution test was performed in conformity with Method 2 (Paddle method) of the Japanese Pharmacopoeia (JP). As the test solution, 900 ml of water was used. The paddle speed was set to 50 rpm. The Composition A prepared in Example 1 was added to the test solution and after 5, 15, 30, 60, 90 and 120 minutes, 0.3 ml aliquots of the test solution were taken as samples. Each sample was centrifuged at 10000 rpm for 3 minutes and 0.1 ml of the supernatant was taken into a plastic tube containing 0.4 ml of methanol. After blending, the mixture was filtered through a 0.5 μm filter and analyzed by high-performance liquid chromatography. Using the Composition A of Example 1, the above procedure was repeated for a total of 3 times (n=3).

Figure 1:
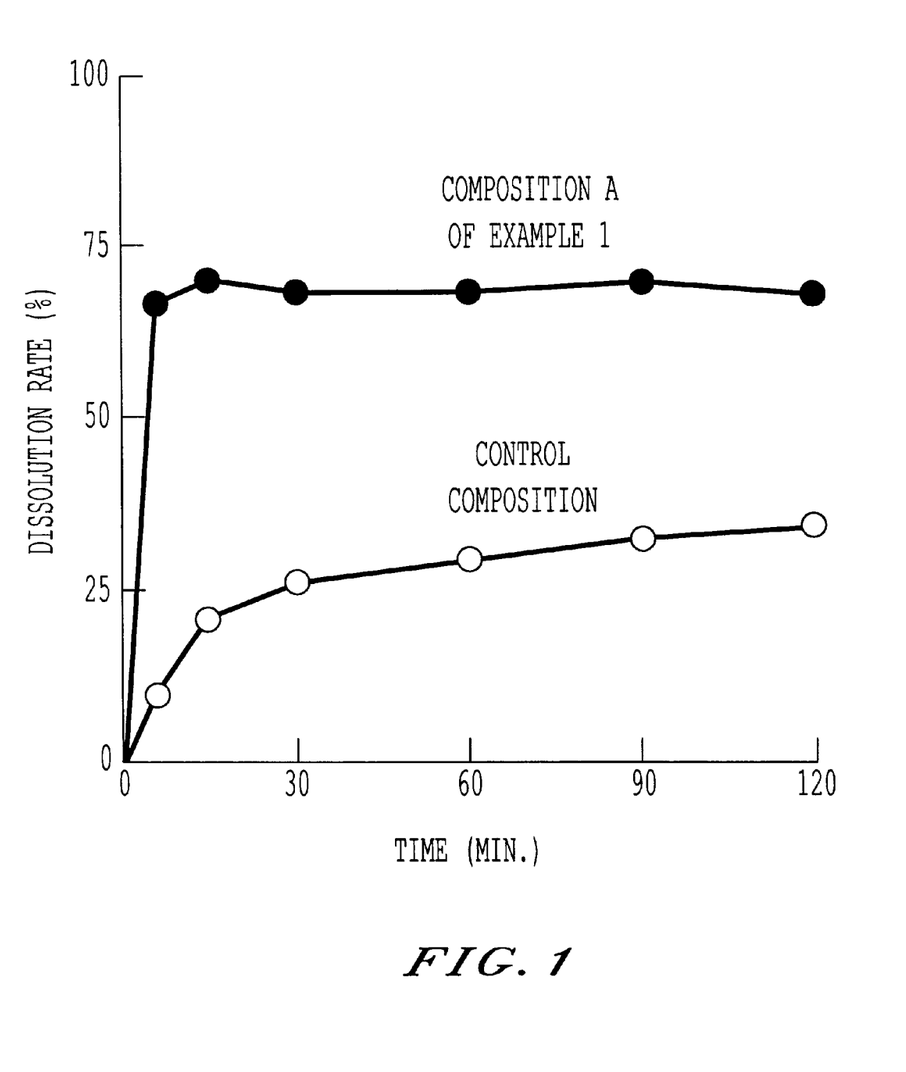
FIG. 1 is a diagram showing the results of a dissolution test by the paddle method.

The results are presented in FIG. 1.

As a control composition, a solid dispersion (composed of bulk powders of compound M (10 mg) which were prepared in the same manner as Example 4 of Japanese Tokkyo Kokai Koho S62-277321, hydroxypropylmethyl-cellulose (40 mg) and low substituted hydroxypropylcellulose (50 mg)) was used.

It is clear from the plots in FIG. 1 that the composition of the present invention has very satisfactory dissolution property.

EXAMPLE 5 (Evaluation of oral absorbability)
(1) Test Method

The following test composition and control composition were respectively administered orally to male beagle dogs (3~6 per group) for comparison of oral absorbability. The body weights of dogs were about 12 kg, and the animals were deprived of food for 24 hours before dosing (dosage as FK506=1 mg/dog). However, drinking water was available throughout the experiment. The dosage of the composition was carried out.around 9:30 a.m. and 40 ml of water was given at the same time. At predetermined intervals after dosing, 1 ml of blood was drawn from the forearm vein using a sterilized syringe into a heparin-containing plastic tube and stored at about −80° C. until determination of drug concentration. The whole blood concentration of the active substance was determined by the FK506-specific enzyme immunoassay (EIA) which was well known from Japanese Tokkyo Kokai Koho H1-92659. The maximum blood concentration (Cmax) was the maximum value of whole blood drug concentrations at respective time-points of determination and the area under the blood concentration-time curve (AUC) was calculated by the trapezoid method.

In addition, as an indicator of variation in oral absorbability, the CV value (standard deviation/mean) was also calculated. The results are presented in Table 1.

(2) Test Compositions

Composition According to Example 3 (19)

Control Composition

A composition (1 mg capsule) according to the following formula as prepared in the same manner as Examples 1 and 2 of WO 91/19495 (by adding (e) and (f) to a solid dispersion of (a)–(d) and encapsulating the mixture)

| | |
|---|---|
| (a) FK506 | 1 mg |
| (b) Hydroxypropylmethylcellulose | 1 mg |
| (c) Lactose | 2 mg |
| (d) Croscarmellose sodium | 1 mg |
| (e) Lactose | 59.35 mg |
| (f) Magnesium stearate | 0.65 mg |

TABLE 1

| Composition | Cmax | | $AUC_{0-8\ hr}$ (ng · hr/ml) | |
|---|---|---|---|---|
| | Mean | CV (%) | Mean | CV (%) |
| Example 3 (19) | 5.1 | 30 | 14.9 | 20 |
| Control | <3.0 | >50 | <5.0 | >50 |

It is clear from Table 1 that the pharmaceutical composition of the present invention has an excellent oral absorbability with high absorption and less variation in said absorption.

The patents, patent applications and publications cited herein are incorporated by reference.

Effect of the Invention

The pharmaceutical composition of the present invention is a solid dispersion having various favorable characteristics such as good stability, good workability, high dissolution property and/or an excellent oral absorbability with high absorption and/or less variation in said absorption. The present invention has enabled the provision of oral dosage forms for compounds, for which any attempt in the past to develop oral products has to be abandoned because of their poor solubility in water or poor absorbability after oral administration or whose potential utility as medicines have not sufficiently been performed heretofore.

The composition of the invention can be administered by various routes, for example externally, parenterally, or by administering into the eye or the nostrils. For oral administration, the composition is ingested directly as capsules, tablets, granules, fine granules, or some other dosage form or it is beforehand dispersed in water, a juice, etc. and ingested in a liquid form. For external application, the composition can be dispersed in water or the like medium and applied in the form of a lotion. For use as an injection, the composition is dispersed in water, saline, or the like and administered. For use as nose-drops, the composition is dispersed in water beforehand and administered into the nostrils. For use as an ophthalmic solution, the composition is dispersed in water, an isotonic buffer solution, or the like and instilled in the eye.

Furthermore, by judicious selection of species of respective components, particularly solid carriers, the dissolution rate and/or release rate can be controlled to provide sustained-release compositions.

When said tricyclic compound (I) is used as the water-insoluble medicinally active substance, the pharmaceutical composition of the present invention is useful for the treatment and prevention of the following diseases and conditions because of the pharmacologic activities possessed by said tricyclic compound (I).

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

and infections caused by pathogenic microorganisms (e.g. Aspergillus fumigatus, Fusarium oxysporum, Trichophyton asteroides, etc.).

Furthermore, pharmaceutical preparations of said tricyclic compound (I) are useful for the therapy and prophylaxis of the following diseases.

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca(dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilic gastroenteritis, mastocytosis, Crohn's disease and ulcerative colitis);

food-related allergic diseases with symptomatic manifestation remote from the gastrointestinal tract (e.g. migrain, rhinitis and eczema);

renal diseases (e.g. intestitial nephritis, Goodpasture's syndrome, hemolytic uremic syndrome, and diabetic nephropathy);

nervous diseases (e.g. multiple myositis, Guillain-Barre syndrome, Meniere's disease, multiple neuritis, solitary neuritis, cerebral infarction, Alzheimer's diseases Parkinson's diseases amyotrophic lateral sclerosis (ALS) and radiculopathy);
cerebral ischemic disease (e.g., head injury, hemorrhage in brain(e.g., subarachnoid hemorrhage, intracerebral hemorrhage), cerebral thrombosis, cerebral embolism, cardiac arrest, stroke, transient ischemic attack (TIA), hypertensive encephalopathy);
endocrine diseases (e.g. hyperthyroidism, and Basedow's disease);
hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);
bone diseases (e.g. osteoporosis);
respiratory diseases (e.g. sarcoidosis, pulmonary fibrosis, and idiopathic interstitial pneumonia);
skin diseases (e.g. dermatomyositis, leukoderma vulgaris, ichthyosis vulgaris, photosensitivity, and cutaneous T-cell lymphoma);
circulatory diseases (e.g. arteriosclerosis, atherosclerosis, aortitis syndrome, polyarteritis nodosa, and myocardosis);
collagen diseases (e.g. scleroderma, Wegener's granuloma, and Sjogren's syndrome);
adiposis;
eosinophilic fasciitis;
periodontal diseases (e.g. damage to gingiva, periodontium, alveolar bone or substantia ossea dentis);
nephrotic syndrome (e.g. glomerulonephritis);
male pattern alopecia, alopecia senile;
muscular dystrophy;
pyoderma and Sezary syndrome;
chromosome abnormality-associated diseases (e.g. Down's syndrome);
Addison's disease;
active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)):
intestinal diseases (e.g. endotoxin shock, pseudomembranous colitis, and drug- or radiation-induced colitis):
renal diseases (e.g. ischemic acute renal insufficiency, chronic renal failure):
pulmonary diseases (e.g. toxicosis caused by pulmonary oxygen or drugs (e.g. paracort, bleomycin, etc.), lung cancer, and pulmonary emphysema):
ocular diseases (e.g. cataracta, iron-storage disease (siderosis bulbi), retinitis, pigmentosa, senile plaques, vitreous scarring, corneal alkali burn):
dermatitis (e.g. erythema multiforme, linear immunoglobulin A bullous dermatitis, cement dermatitis):
and other diseases (e.g. gingivitis, periodontitis, sepsis, pancreatitis, and diseases caused by environmental pollution (e.g. air pollution), aging, carcinogen, metastasis of carcinoma, and hypobaropathy)];
diseases caused by histamine release or leukotriene C4 release;
restenosis of coronary artery following angioplasty and prevention of postsurgical adhesions;
Autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), orpolychondritis);

Human Immunodeficiency Virus (HIV) infections AIDS;

allergic conjunctivitis;

hypertrophic cicatrix and keloid due to trauma, burn, or surgery.

In addition, the tricyclic compound (I) has liver regenerating activity and/or activities of stimulating hypertrophy and hyperplasia of hepatocytes.

Therefore, the pharmaceutical composition of the present invention is useful for the therapy and prophylaxis of liver diseases [e.g. immunogenicdiseases (e.g. chronicautoimmuneliver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

And further, the present composition is useful for preventing or treating various diseases because of its useful pharmacological activity such as augmenting activity of chemotherapeutic effect, activity of cytomegalovirus infection, anti-inflammatory activity, inhibiting activity against peptidyl-prolyl isomerase or rotamase, antimalarial activity, antitumor activity, and so on.

Additionally, *Streptomyces tsukubaensis* No. 9993 (accession number FERM BP-927), which is described in the page 5, lines 10–11, of the present description, was deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan (date of deposit: Oct. 5, 1984). Further, *Streptomyces hygroscopicus* subsp. yakushimaensis No. 7238 (accession number FERM BP-928), which is described in the page 5, lines 11–12 of the present description, was also deposited with National Institute of Bioscience and Human Technology Agency of Industrial Science and Technology (date of deposit: Jan. 12, 1985).

What is claimed is:
1. A solid dispersion comprising a tricyclic compound (I) of the following general formula or a pharmacologically acceptable salt thereof:

(I)

wherein each of adjacent pairs of $R^1$ and $R^2$, $R^3$ and $R^4$ or $R^5$ and $R^6$ independently
(a) are two adjacent hydrogen atoms, or
(b) may form another bond formed between the carbon atoms to which they are attached,
and further, $R^2$ may be an alkyl group;

$R^7$ is a hydrogen atom, a hydroxy group, a protected hydroxy group or an alkoxy group, or an oxo group together with $R^1$, each of $R^8$ and $R^9$ is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;

X is an oxo group, (a hydrogen atom and a hydroxy group), (a hydrogen atom and a hydrogen atom), or a group represented by the formula —CH$_2$O—;

Y is an oxo group, (a hydrogen atom and a hydroxy group), (a hydrogen atom and a hydrogen atom), or a group represented by the formula N—NR$^{11}$R$^{12}$ or N—OR$^{13}$;

each of $R^{11}$ and $R^{12}$ is independently a hydrogen atom, an alkyl group, an aryl group or a tosyl group;

each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;

each of $R^{20}$ and $R^{21}$ is independently an oxo group or ($R^{20}$a and a hydrogen atom) or ($R^{21}$a and a hydrogen atom) in which each of $R^{20}$a and $R^{21}$a is independently a hydroxy group, an alkoxy group or a group represented by the formula —OCH$_2$OCH$_2$CH$_2$OCH$_2$, or $R^{21}$a is a protected hydroxy group, or $R^{20}$a and $R^{21}$a may together represent an oxygen atom in an epoxide ring;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl and a group of the formula —CH$_2$Se(C$_6$H$_5$); and a pharmaceutically acceptable surfactant selected from the group consisting of polyoxyethylene hydrogenated castor oil, sucrose fatty acid esters, propylene glycol fatty acid mono- or di-esters, and polyoxyethylene sorbitan fatty acid esters, or a combination of two or more of these surfactants;

and a pharmaceutically acceptable solid carrier selected from the group consisting of water-soluble polymers, saccharides, and light anhydrous silicic acid, or a combination of two or more of these solid carriers;

in which the weight ratio of the tricyclic compound (I), the surfactant and the solid carrier is 1:01~100:1~300.

2. The solid dispersion according to claim 1, wherein the tricyclic compound (I) is the one therein each of adjacent pairs of $R^3$ and $R^4$ or $R^5$ and $R^6$ independently may form another bond formed between the carbon atoms to which they are attached;

each of $R^8$ and $R^{23}$ is independently a hydrogen atom;
$R^9$ is a hydroxy group;
$R^{10}$ is a methyl group, an ethyl group, a propyl group or an allyl group;
X is (a hydrogen atom and a hydrogen atom) or an oxo group;
Y is an oxo group;
each of $R^{14}$, $R^{15}$, $R^{16}$, $R^{17}$, $R^{18}$, $R^{19}$, and $R^{22}$ is a methyl group;
each of $R^{20}$ and $R^{21}$ is independently ($R^{20}$a and a hydrogen atom)
or ($R^{21}$a and a hydrogen atom) in which each of $R^{20}$a and $R^{21}$a is a hydroxy group or an alkoxy group, or R21a is a protected hydroxy group; and
n is an integer of 1 or 2.

3. The solid dispersion according to claim 2, wherein said tricyclic compound (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

4. A process for producing the solid dispersion of claim 1, which comprises (1) a step of adding solid carrier(s) to organic solvent(s) dissolving a water-insoluble medicinally active substance and surfactant(s), and kneading the mixture, and (2) a step of, after removing the organic solvent(s), drying the resultant residue and pulverizing the same.

5. The solid dispersion of claim 1, in which the surfactant is a combination of polyoxyethylene hydrogenated castor oil and propylene glycol fatty acid mono- or di-esters.

6. The solid dispersion of claim 1, in which the solid carrier is selected from the group consisting of hydroxypropylmethylcellulose, polyvinyl pyrrolidone, lactose, light anhydrous silicic acid, or a combination of two or more of these ingredients.

7. The solid dispersion of claim 1, in which the weight ratio of the tricyclic compound (I), the surfactant, and the solid carriers is 1:4–40:10–100.

8. The solid dispersion of claim 1, further comprising a disintegrator.

* * * * *